United States Patent
Jin et al.

(10) Patent No.: US 10,647,581 B2
(45) Date of Patent: May 12, 2020

(54) BIOELECTROCHEMICAL METHODS AND SYSTEMS FOR EFFICIENT PRODUCTION OF GRAPHENE OXIDE AND HYDROGEN

(71) Applicant: BEGO Technologies, Ltd., Hong Kong (CN)

(72) Inventors: Song Jin, Fort Collins, CO (US); Ran Li, Superior, CO (US); Paul Fallgren, Fort Collins, CO (US); Kylan Jin, Fort Collins, CO (US)

(73) Assignee: BEGO TECHNOLOGIES, LTD., Hong Kong (HK)

( * ) Notice: Subject to any disclaimer, the term of this patent is extended or adjusted under 35 U.S.C. 154(b) by 0 days.

(21) Appl. No.: 15/772,380

(22) PCT Filed: Oct. 31, 2016

(86) PCT No.: PCT/US2016/059724
§ 371 (c)(1),
(2) Date: Apr. 30, 2018

(87) PCT Pub. No.: WO2017/075592
PCT Pub. Date: May 4, 2017

(65) Prior Publication Data
US 2018/0319666 A1    Nov. 8, 2018

Related U.S. Application Data

(60) Provisional application No. 62/249,227, filed on Oct. 31, 2015.

(51) Int. Cl.
*C25B 1/00*        (2006.01)
*C25B 3/04*        (2006.01)
(Continued)

(52) U.S. Cl.
CPC .......... *C01B 32/198* (2017.08); *C01B 32/184* (2017.08); *C12P 3/00* (2013.01);
(Continued)

(58) Field of Classification Search
CPC ................................... C25B 1/00; C25B 3/04
(Continued)

(56) References Cited

U.S. PATENT DOCUMENTS

2012/0129736 A1    5/2012  Tour et al.
2013/0306488 A1*  11/2013  Taniguchi ............... B01J 27/04
                                                          205/440
(Continued)

FOREIGN PATENT DOCUMENTS

CN    102745683 A    10/2012
CN    102745684 A    10/2012
(Continued)

OTHER PUBLICATIONS

Shukla et al., "Biological Fuel Cells and Their Applications," Current Science (Aug. 25, 2004), vol. 87, No. 4, pp. 455-468. (Year: 2004).*
(Continued)

*Primary Examiner* — Edna Wong
(74) *Attorney, Agent, or Firm* — Santangelo Law Offices, P.C.

(57) ABSTRACT

Graphene oxide (GO) is an emerging material for energy, environmental, and many other applications which in the past has been produced using chemical processes involving high-energy consumption and hazardous chemicals. Embodiments of the present invention focus on bioelectrochemical systems (BES) having microorganism(s), an anode (11) and cathode (14) to produce GO (13) from graphite, coal, and other carbonaceous materials under ambient conditions without chemical amendments. In some embodi-
(Continued)

ments, value-added organic compounds (17) and even $H_2$ (16) can be produced.

22 Claims, 11 Drawing Sheets

(51) Int. Cl.
| | | |
|---|---|---|
| C01B 32/198 | (2017.01) | |
| C25B 11/02 | (2006.01) | |
| C25B 9/06 | (2006.01) | |
| C25B 1/04 | (2006.01) | |
| C01B 32/184 | (2017.01) | |
| C12P 3/00 | (2006.01) | |
| C25B 11/04 | (2006.01) | |

(52) U.S. Cl.
CPC .................. *C25B 1/00* (2013.01); *C25B 1/04* (2013.01); *C25B 3/04* (2013.01); *C25B 9/06* (2013.01); *C25B 11/02* (2013.01); *C25B 11/0489* (2013.01); *C01B 2204/22* (2013.01)

(58) Field of Classification Search
USPC ................................................ 205/413, 555
See application file for complete search history.

(56) References Cited

U.S. PATENT DOCUMENTS

| | | | |
|---|---|---|---|
| 2014/0315046 A1 | 10/2014 | Yoshida et al. | |
| 2015/0060297 A1 | 3/2015 | Wei et al. | |
| 2015/0259669 A1* | 9/2015 | May | C12N 1/20 |
| | | | 435/135 |
| 2016/0022827 A1 | 1/2016 | Chan et al. | |

FOREIGN PATENT DOCUMENTS

| | | | | | |
|---|---|---|---|---|---|
| KR | 20110065971 A | * | 6/2011 | ............... | C25B 1/00 |
| KR | 20110065971 A | | 6/2011 | | |
| WO | 2012/167218 A2 | | 12/2012 | | |
| WO | 2014196825 A1 | | 12/2014 | | |
| WO | 2017/075592 A1 | | 5/2017 | | |

OTHER PUBLICATIONS

Villano et al., "Bioelectrochemical Reduction of CO2 to CH4 via Direct and Indirect Extracellular Electron Transfer by a Hydrogenophilic Methanogenic Culture," Bioresource Technology (2010), vol. 101, pp. 3085-3090. (Year: 2010).*
Tang et al., "In Situ Formation of Graphene Layers on Graphite Surfaces for Efficient Anodes of Microbial Fuel Cells," Biosensors and Bioelectronics (2015), vol. 71, pp. 387-395. (Year: 2015).*
Zhang et al. ("Generation of Electricity and Analysis of Microbial Communities in Wheat Straw Biomass-Powered Microbial Fuel Cells," Applied and Environmental Microbiology (Jun. 2009), vol. 75, No. 11, pp. 3389-3395) (Year: 2009).*
Kreig et al., "Reactor Concepts for Bioelectrochemical Synthesis and Energy Conversions," Trends in Biotechnology (Dec. 2014), vol. 32, No. 12, pp. 645-655. (Year: 2014).*
Tremblay et al., "Electrifying Microbes for the Production of Chemicals," Frontiers in Microbiology (Mar. 2015), vol. 6, Article 201, pp. 1-10. (Year: 2015).*
Takanezawa et al., "Factors Affecting Electric Output from Rice-Patty Microbial Fuel Cells," Biosci. Biotechol. Biochem. (2010), vol. 74, No. 6, pp. 1271-1273. (Year: 2010).*
Rashid et al., "Enhanced Electricity Generation by Using Algae Biomass and Activated Sludge in Microbial Fuel Cell," Science of the Total Environment (2013), 456-457, pp. 91-94. (Year: 2013).*
Villano et al, ("Bioelectrochennical Reduction of CO2 to CH4 via Direct and Indirect Extracellular Electron Transfer by a Hydrogenophilic Methanogenic Culture," Bioresource Technology (2010), vol. 101, pp. 3085-3090. (Year: 2010).*
Ren et al., "Bioelectrochennical Oxidation of Graphite Drives Graphene Production and Electrosynthesis," Abstract of Papers, 249th ACS National Meeting & Exposition, Denver, CO, United States, Mar. 22-26, 2015 (2015), ENFL-201, pp. 1-2. (Year: 2015).*
Watanabe et al., "Effect of Initial pH on Formation of Hollow Calcium Carbonate Particles by Continuous CO2 Gas Bubbling into CaCl2 Aqueous Solution," Advanced Powder Technology (2009), vol. 20, pp. 89-93. (Year: 2009).*
Hu et al., "Hydrogen Production in Single-Chamber Tubular Microbial Electrolysis Cells Using Non-Precious-Metal Catalysts," International Journal of hydrogen Energy (2009), vol. 34, pp. 8535-8542. (Year: 2009).*
Srikanth et al., "Enzymatic Electrosynthesis of Formate Through CO2 Sequestration/Reduction in a Bioelectrochemical System (BES)," Biosource Technology (2014), vol. 165, pp. 350-354. (Year: 2014).*
Friman et al., "Phenol Degradation in Bio-Electrochemical Cells," International Biodeterioration & Biodegradation (2013), vol. 84, pp. 155-160. (Year: 2013).*
Park, Sungjin and Rodney Ruoff, Chemical methods for the production of graphenes. Nature Nanotechnology vol. 4, Review Article, published Mar. 29, 2009. 9 pages.
Lu, L et al., Graphene oxide and H2 production from bioelectrochemical graphite oxidation. Scientific Reports. vol. 5, published Nov. 17, 2015. www.nature.com/scientificreports, 11 pages.
Lu, L, et al. Supplementary Information for Graphene oxide and H2 production from bioelectrochemical graphite oxidation., published Nov. 17, 2015. 6 pages.
U.S. Appl. No. 62/249,227, filed Oct. 31, 2015. First Named Inventor: Song Jin.
International Application No. PCT/US16/059724 filed Oct. 31, 2016. First Named Inventor: Jin.
International Application No. PCT/US16/059724 filed Oct. 31, 2016. First Named Inventor: Jin. International Search Report dated Dec. 30, 2016. 3 pages.
International Application No. PCT/US16/059724 filed Oct. 31, 2016. First Named Inventor: Jin. International Search Report dated Dec. 30, 2016. 4 pages.
European Search Report, European Patent Application No. 16861043.4-1108 / 3368476, dated May 21, 2019, 10 pages.
Shukla, et al., "Biological fuel cells and their applications," Current Science, vol. 87, No. 4, Apr. 25, 2004, 14 pages.

* cited by examiner

BIOELECTROCHEMICAL METHODS AND SYSTEMS FOR EFFICIENT PRODUCTION OF GRAPHENE OXIDE AND HYDROGEN

PRIORITY CLAIM

This application is the United States National Phase of PCT International Application Number PCT/US2016/059724, filed Oct. 31, 2016, which claims priority to and the benefit of U.S. Provisional Application No. 62/249,227 filed Oct. 31, 2015 both applications are hereby incorporated by reference herein in their entirety.

FIELD OF THE INVENTION

Embodiments of the present invention relate to efficient production of graphene oxide. More specifically, the invention relates to the utilization of systems and methods involving microbes, electricity, and bioelectrochemical reactions to produce graphene oxide compounds and even hydrogen gas from graphite, coal, and other carbonaceous material perhaps under ambient or even mild conditions.

BACKGROUND OF INVENTION

Graphene and its precursor graphene oxide ("GO") belong to the frontier of new materials having unique electrical, thermal, or even mechanical properties with wide application potentials. To date, contemporary graphene production involves chemical oxidation of graphite to graphite oxide or graphene oxide under high temperature and other extreme reaction conditions, followed by reducing GO to graphene using chemical, thermal, or even electrochemical methods. GO not only is an important precursor for mass production of graphene-based materials, it may also have great potentials to be used in many areas, such as but not limited to, electronics, optoelectronics, bio-nanotechnology, renewable energy, membrane research, environmental applications, or the like. In the past, GO has been mainly synthesized by chemical oxidation based on the Hummers, Brodie, or even Staudenmaier methods. All of these chemical methods use concentrated acids, such as sulfuric acid ($H_2SO_4$) and nitric acid ($HNO_3$), or even toxic reagents, such as potassium dichromate ($K_2Cr_2O_7$), potassium permanganate ($KMnO_4$), or even explosive potassium chlorate ($KClO_3$) to oxidize graphite to GO, and the production procedure can be expensive, dangerous, and even non-sustainable.

Certain electrochemical exfoliation of graphite to GO or graphene has been attempted in ionic liquids such as aqueous acids and inorganic salt solutions under between about 7V to about 20V in voltage, and the products were reported with different levels of defects in the crystal lattice and even oxygen-doping. Certain biological methods have also been attempted and reports show that microorganisms can oxide dispersed graphite to graphite oxide nanosheets, but external carbon sources and oxygen were needed and the reaction rate was too low to have commercial value.

It is thus a need to provide new systems and methods which can produce graphene or GO at rates of commercial merit, under ambient conditions, under mild conditions, or the like.

SUMMARY OF INVENTION

The present invention discloses methods and systems for efficient production of graphene oxide and even hydrogen using bioelectrochemical systems.

It is an object of the present invention to provide a bioelectrochemical method to produce both GO and hydrogen gas under ambient conditions by using graphite, coal and/or other carbonaceous materials, or the like as feedstock.

It is another object of the present invention that bioelectrochemical system device may: be in a container reactor configuration of any geographic shape; include an anode in any form such as but not limited to solid chunk, rod, particles, powder, or the like perhaps of graphite, coal, or other carbonaceous materials; include a cathode made of any conductive material such as but not limited to stainless steel, carbon, graphite, alloy metals, or the like, in any form; and may even include a solution having a mixture of microorganisms, common nutrients, and perhaps even trace elements, or the like, or any combination thereof, that may keep the microbes viable. The microorganisms may include aerobic, facultative, and perhaps even anaerobic species, or any combination thereof, or the like that may carry different metabolic reactions. The microorganisms can be inoculated perhaps by using municipal sludge, soil, any other matrices such as those containing such mixture of microbial consortia, any combination thereof or the like.

Naturally, further objects, goals and embodiments of the invention are disclosed throughout other areas of the specification, claims, and figures.

BRIEF DESCRIPTION OF DRAWINGS

The following descriptions and referenced drawings are for selected embodiments of the present invention. Naturally, changes may be made to the disclosed embodiments while still falling within the scope and spirit of the present invention and the patent granted.

FIGS. 1 and 2 show examples of two and three-electrode bioelectrochemical system ("BES").

DETAILED DESCRIPTION OF PREFERRED EMBODIMENTS

The basic concepts of the present invention may be embodied in a variety of ways. It involves both scrubber techniques as well as devices to accomplish the appropriate scrubber. In this application, the scrubber techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Embodiments of the present invention include at least one bioelectrochemical system (BES), which can produce exfoliated graphite oxide and graphene oxide (GO) from rods, solid rods, pellets, powder suspension or liquid suspension filling the reactor, or even powder of graphite, coal, or other carbonaceous materials, or the like, or any combination thereof. The GO production may be accompanied with the production of value-added $H_2$ and perhaps even organic compounds. Embodiments of the present invention can eliminate the use of expensive and even potentially hazardous chemicals for bulk GO production. These may even present the possibility of using abundant graphite as an electron source for co-production of clean energy and perhaps even chemicals.

The present invention may provide a bioelectrochemical system (1) for producing graphene oxide comprising a biochemical reactor comprising at least one graphite containing anode; at least one cathode comprising a conductive material; at least one transmission line connecting a load between said at least one graphite containing anode and said at least one cathode; at least one direct current electricity source connected to said at least one transmission line; at least one microbial population capable of interacting with said at least one graphite containing anode and generating graphene oxide; and perhaps even a graphene oxide collector (2) capable of collecting graphene oxide from said biochemical reactor. The present invention may provide a bioelectrochemical method for producing graphene oxide comprising the steps of providing at least one biochemical reactor, providing at least one graphite containing anode and at least one cathode in each of said at least one biochemical reactor; wherein said at least one cathode comprises a conductive material; connecting a load between said at least one graphite containing anode and said at least one cathode with a transmission line; providing at least one direct current electricity source connected to said transmission line; providing at least one microbial population in each of said at least one biochemical reactor; interacting said graphite containing anode with said microbial species resulting in production of graphene oxide, carbon dioxide ($CO_2$) and electrons; transferring said electrons from said anode to said cathode via said transmission line; microbiologically reducing protons and said $CO_2$ at said cathode resulting in production of $H_2$ and organic compounds; and perhaps even collecting said graphene oxide from said biochemical reactor. Other embodiments of the present invention may provide a bioelectrochemical system for producing graphene oxide comprising a biochemical reactor comprising at least one graphite containing anode; at least one cathode comprising a conductive material; at least one transmission line connecting a load between said at least one graphite containing anode and said at least one cathode; at least one direct current electricity source connected to said at least one transmission line; at least one type of enzyme capable of interacting with said at least one graphite containing anode and generating graphene oxide; and perhaps even a graphene oxide collector capable of collecting graphene oxide from said biochemical reactor. Enzymes may be used separately in a biochemical reactor perhaps even without the presence of microorganisms. As such at least one biological activity such as enzymes or the like may be capable of interacting with a graphite containing anode to generate graphene oxide.

Figure 1:
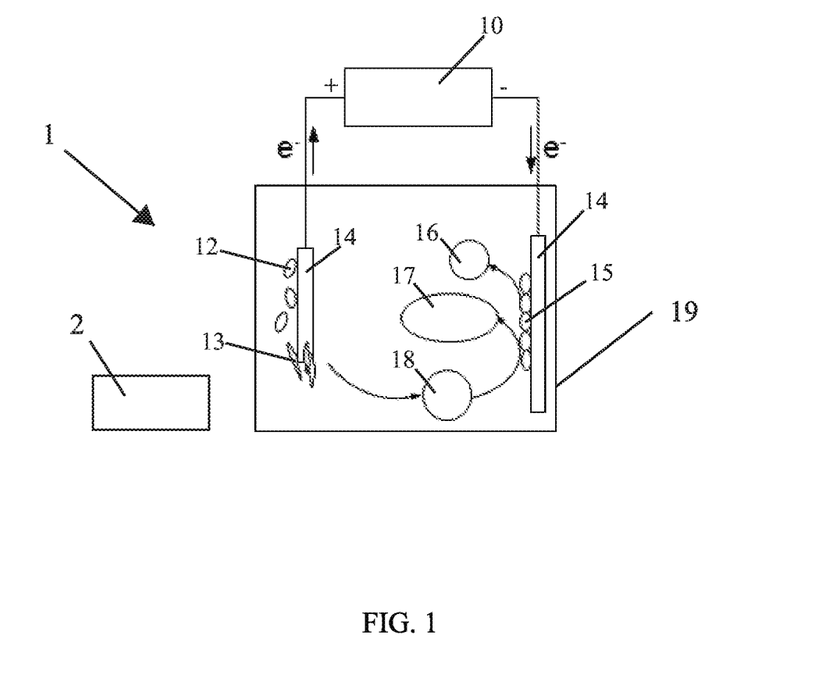
FIG. 1 shows an example of reaction mechanisms in BES, including microbial catalyzed GO production on an anode and microbial electrosynthesis on a cathode, in accordance with various embodiments of the present invention.
Figure 2:
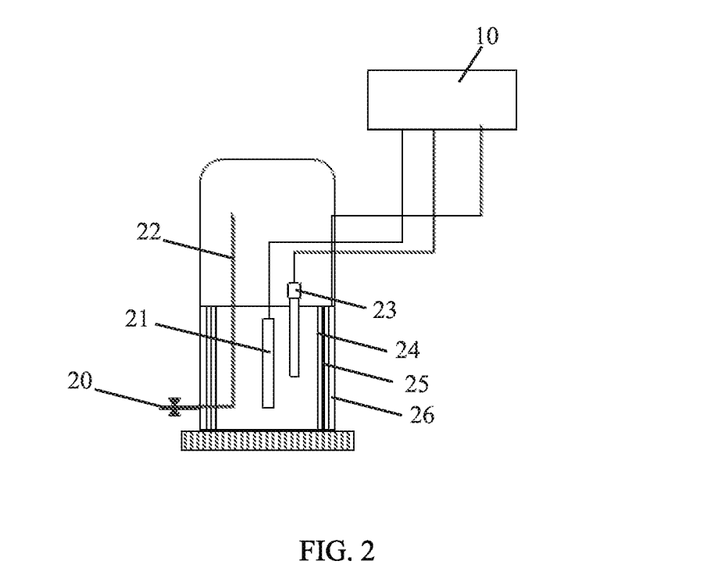
FIG. 2 shows an example configuration of water sealed BES reactors in accordance with various embodiments of the present invention.

An example of use of BES with a graphite rod as an anode is shown in FIGS. 1 and 2. An anode (11) perhaps a graphite rod electrode may be exfoliated by at least one microbial population (12) to produce graphene oxide (13) (e.g., bioelectrochemical graphene oxide ("BEGO")) in a colloidal suspension, $CO_2$, (18) and electrons, and the like in at least one biochemical reactor (19). In addition to graphene oxide, graphene and perhaps even graphite oxide may be produced perhaps in small amounts. Electrons, perhaps controlled with a direct current electricity source (10) such as a potentiostat, derived from anode oxidation may be transferred to a cathode (14) such as a biocathode, where $H_2$ (16) and even organics (17) may be produced such as by microbial (15) reduction of protons and $CO_2$, respectively as shown in FIG. 1. In addition to the electricity-driven reduction of $CO_2$, a cathode may involve microbially catalyzed synthesis of chemical compounds in an electrochemical system perhaps using direct or even indirect electron transfer from the electrode to the microorganisms. By coupling biological with electrochemical mechanisms, a graphite anode in a BES may be oxidized and even exfoliated into BEGO colloidal suspension, perhaps by interaction of with at least one microbial population, at a faster rate than abiotic controls. A graphene oxide collector (2) may be any kind of apparatus or method where the graphene oxide and perhaps even graphene and/or graphite oxide may be separated and/or even collected from a cell such as but not limited to a screens, magnets, nets, or the like.

Another non-limiting example of a BES reactor is shown in FIG. 2. Cylindrical glass bottles may be used as a two or even three-electrode reactor system. Each reactor may have an effective volume of about 220 mL (this volume can vary and can even be proportionally changed to other volumes). An anode (21) such as a graphite rod (D about 0.6 cm×L about 5 cm) may be used, and a carbon cloth (about 5 cm×about 10 cm) may serve as a cathode (26). A layer of nonconductive permeable glass fiber (25) and perhaps even a layer of nylon mesh (24) may be placed onto a cathode perhaps as a separator and even a support. An Ag/AgCl reference electrode (23) (e.g., RE-5B, BASi) may be placed in between an anode and a cathode (e.g., 0.198 V vs SHE (a reference electrode, the standard hydrogen electrode, herein referred to as "SHE"). Electrodes may be connected using titanium wires. A potentiostat (10) may be used to poise a cathode (working electrode) at about −0.6V (vs. SHE), where anode may be a counter electrode. The potentials may be reported versus SHE. BES reactors can be inoculated with anaerobic sludge perhaps collected from an anaerobic digester, and the initial medium may include (per liter): about 0.36 g of glucose, about 11.55 g of $Na_2HPO_4.12H_2O$, about 2.77 g of $NaH_2PO_4.2H_2O$, about 0.31 g of $NH_4Cl$, about 0.13 g of KCl, trace materials, vitamins flushed with about 100% $CO_2$ perhaps to reach a constant $CO_2$ content of about ~5.6 mmol in the headspace, or the like. A sampling port (20) and a syringe needle (22) may be included in the reactor. Carbon dioxide may be used as a carbon source for microbial electrosythesis of organics. When current production may be observed, a liquid may be replaced with the same medium but, in some embodiments, without glucose and even a sludge inoculum. The operation may be conducted in anaerobic conditions, and perhaps after each transfer, the liquid and even headspace may be flushed with about 100% $CO_2$. An enrichment stage may be considered complete perhaps when high current, $H_2$ and even organic production may be observed. Thereafter, at least three batch cycles may be operated. In embodiments, to quantify carbon flow, no more $CO_2$ flushing may be conducted during a media change perhaps after the first cycle. An exfoliated anode could be replaced if necessary during this stage. Three reactors were prepared as experiment replicates but were started at different time. The three reactors showed similar operation profiles and one reprehensive time course reactor profile is reported. The GO1, GO2 and GO3 are samples taken from three replicated reactors, respectively. All reactors were operated at room temperature of about 25-2° C. Two abiotic control reactors were operated. One followed the same protocol as the active reactor, with the cathode poised at about −0.6 V (vs. SHE). Another control was setup by poising the anode at about +1.6 V (vs. SHE), which was the maximum anode potential observed in a BES reactor.

Figure 3:
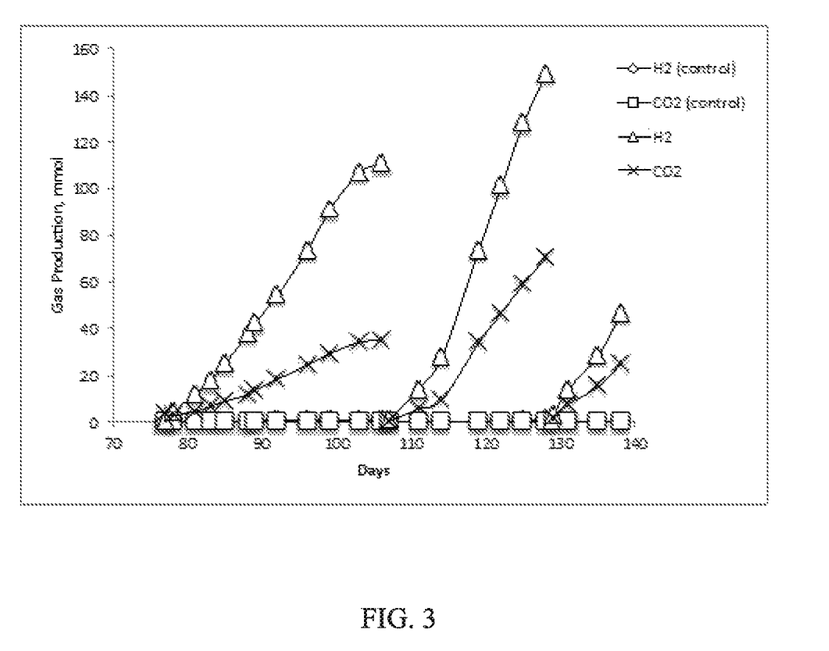
FIGS. 3 and 4 shows a graph of products, which may be generated in a BES using graphite as anode in accordance with various embodiments of the present invention.
Figure 4:
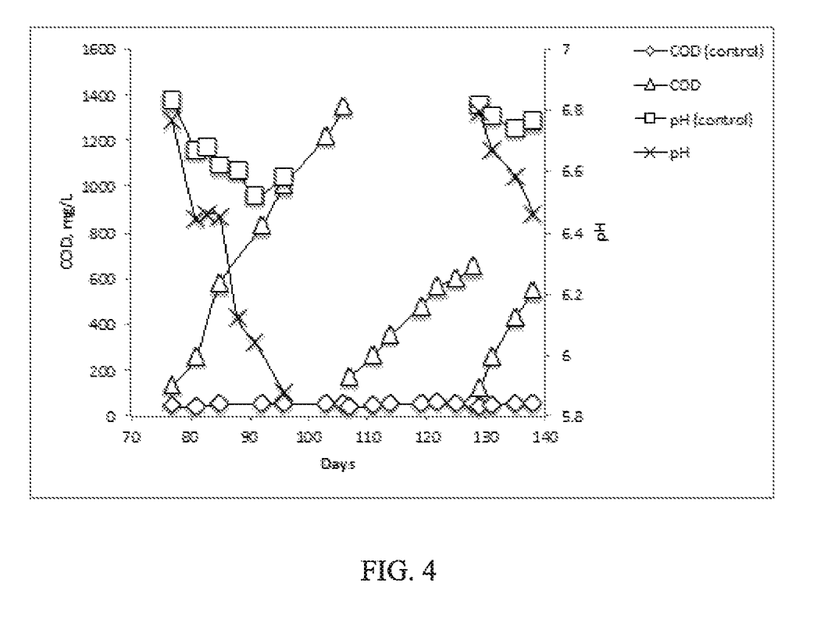

FIGS. 3 and 4 presents an example of the products generation during GO production and microbial electrosynthesis. FIG. 3 shows the gas ($H_2$ and $CO_2$) production in the BES. FIG. 4 shows the changes of COD and pH of the solution. Cathodes were poised at about −0.6 V (vs. SHE). An un-inoculated abiotic reactor with a cathode poised at about −0.6 V vs. SHE was used as control. Data is shown from day 76 to day 138, which may represent repeatable cycles of system performance after microbial acclimation and even enrichment.

Figure 5:
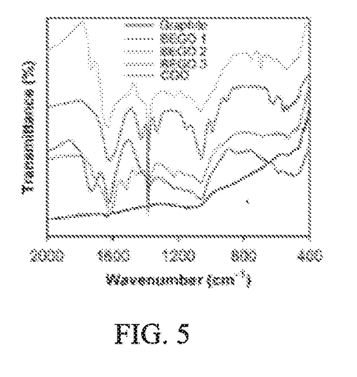
FIG. 5 shows an example FT-IR spectra of BES-produced GO and a commercial GO ("CGO") sample.
Figure 6:
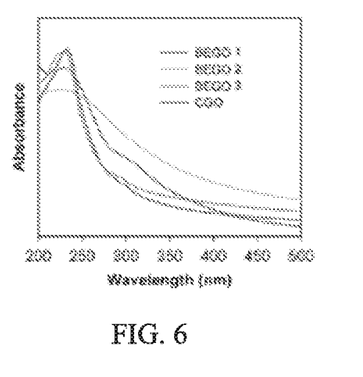
FIG. 6 shows an example UV-vis spectra of BES-produced GO and a commercial sample.
Figure 7:
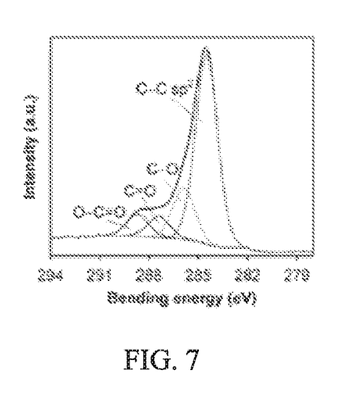
FIG. 7 shows an example XPS of C 1s spectra of a BES-produced GO.
Figure 8:
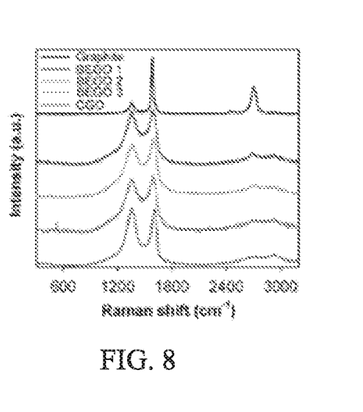
FIG. 8 shows an example Raman spectra of BES-produced GO, graphite and commercial GO.
Figure 9:
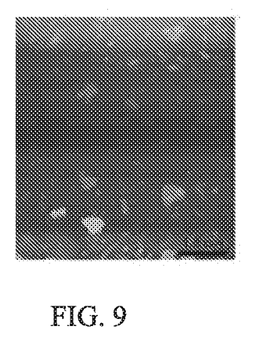
FIG. 9 shows an example AFM image of BEGO samples.
Figure 10:
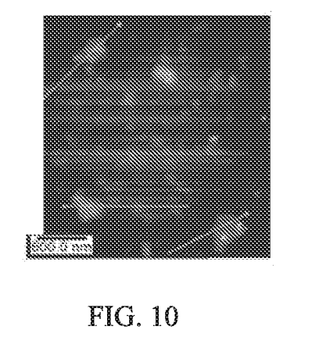
FIG. 10 shows an example AFM zoomed image for the middle region of BEGO samples.
Figure 11:
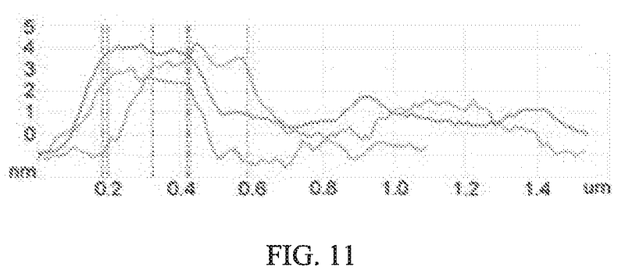
FIG. 11 shows an example AFM cross-section height profile of BEGO samples.
Figure 12:
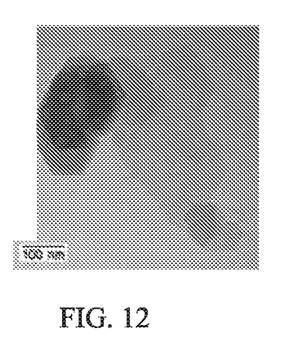
FIG. 12 shows an example TEM of BEGO samples.
Figure 13:
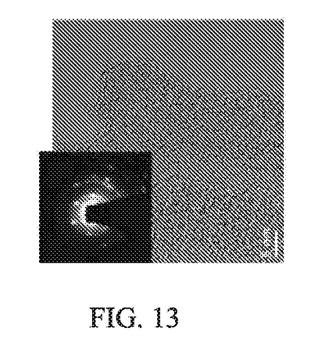
FIG. 13 shows an example HRTEM images of BEGO samples. The inset in FIG. 13 is a selected area electron diffraction ("SAED") pattern.

FIGS. 5-13 shows confirmation and even characterization of examples of BES-produced GO vs. commercial GO samples of a characterization of produced GO. FIG. 5 shows an example FT-IR spectra of BES-produced GO and a commercial GO ("CGO") sample. FIG. 6 shows an example UV-vis spectra of BES-produced GO and a commercial sample. FIG. 7 shows an example XPS of C 1s spectra of a BES-produced GO. FIG. 8 shows an example Raman spectra of BES-produced GO, graphite and commercial GO. FIG. 9 shows an example AFM image. FIG. 10 shows an example AFM zoomed image for the middle region. FIG. 11 shows an example AFM cross-section height profile. FIG. 12 shows an example TEM. FIG. 13 shows an example HRTEM images. The inset in FIG. 13 is a selected area electron diffraction ("SAED") pattern.

Figure 14:
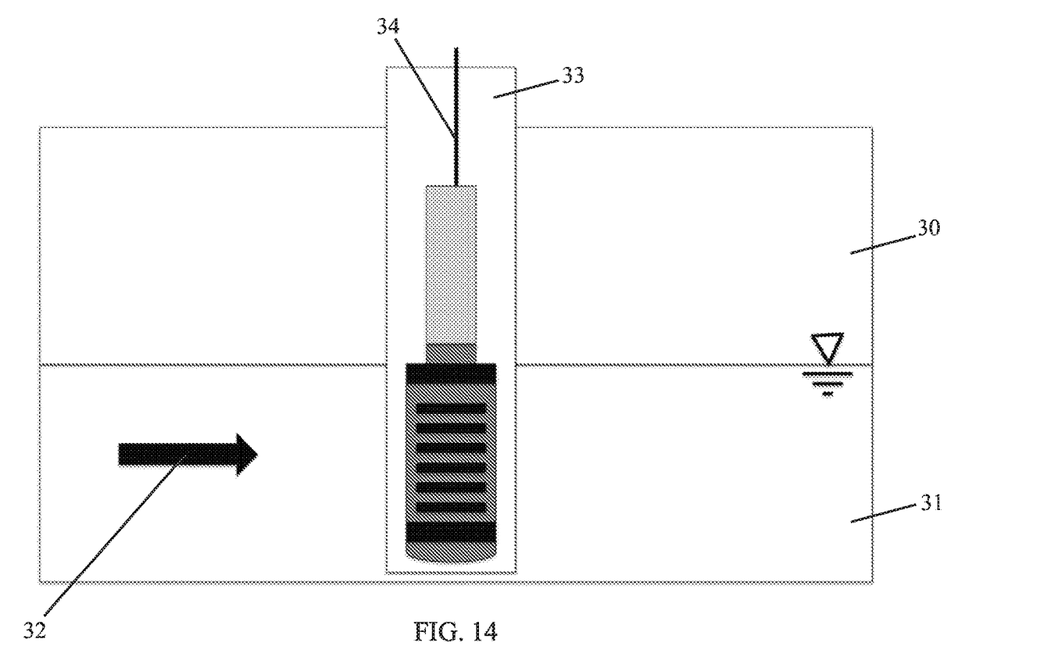
FIG. 14 shows an example drawing of a hollow-tube bioelectrochemical system (BES) inserted into a container perhaps packed with graphite, coal, or other carbonaceous materials in accordance with various embodiments of the present invention.

FIG. 14 is an example of a single BES module that can be inserted into a reactor perhaps packed with solid rods, pellets, or even powder of graphite, coal, or other carbonaceous materials, or the like. It is an example of a hollow-tube bioelectrochemical system (BES) inserted into a container perhaps packed with graphite, coal, or other carbonaceous materials which can be above ground or even in an in-ground pit or void or the like in accordance with various embodiments of the present invention. A perforated casing of the BES may expose an anode to the surrounding carbonaceous materials, which may be immersed in a solution perhaps containing microbial consortia, common nutrients, trace elements, combinations thereof or the like. A reactor may include an unsaturated zone (30) and a saturated zone (31) and may even have a groundwater flow, such as the arrow (32) shown in FIG. 14 representing the direction of groundwater flow. Each BES module (33) may include at least one anode and at least one cathode, perhaps each surrounding a hollow tube (34) or pipe, or the like. The anode may be fixed as the outermost layer surrounding a hollow tube or pipe or the like. A cathode may be fixed as an innermost layer surrounding and even directly in contact with a hollow tube or pipe or the like. The hollow tube or pipe may be perforated perhaps to allow contact with air or oxygen or the like. Possible hollow tube or pipe materials include, but are not limited to, polyvinyl chloride, polymethyl methacrylate, fiberglass, high-density polytetrafluoroethylene, and other plastics. Possible anode materials may include, but are not limited to, carbonaceous materials (man-made or naturally existing), granulated activated carbon, biochar, graphite, coal, petroleum coke, anthracite, carbon clothe, carbon fiber, carbon fiber brush, any combination thereof or the like. Possible cathode materials may include, but are not limited to, fine stainless steel mesh, stainless steel foam, iron filings, stainless steel rod, mesh, stainless steel wool, stainless steel foam, and stainless steel brush, carbon cloth, activated carbon, carbon paper, or the like. The cathode may or may not be coated with a catalyst, which may include, but is not limited to, platinum/carbon (Pt/C) catalyst, iridium catalyst, zinc oxide, lead oxides, titanium oxides (rutile), or the like. On one side, a cathode may be coated with a waterproof but air permeable material, which may include, but is not limited to, polytetrafluoroethylene or poly(dimethylsiloxane). An anode and cathode may be connected to respective leads or even receptacles, where wire connectors may connect a load or even a simple resistor to anodes and cathodes.

Figure 15:
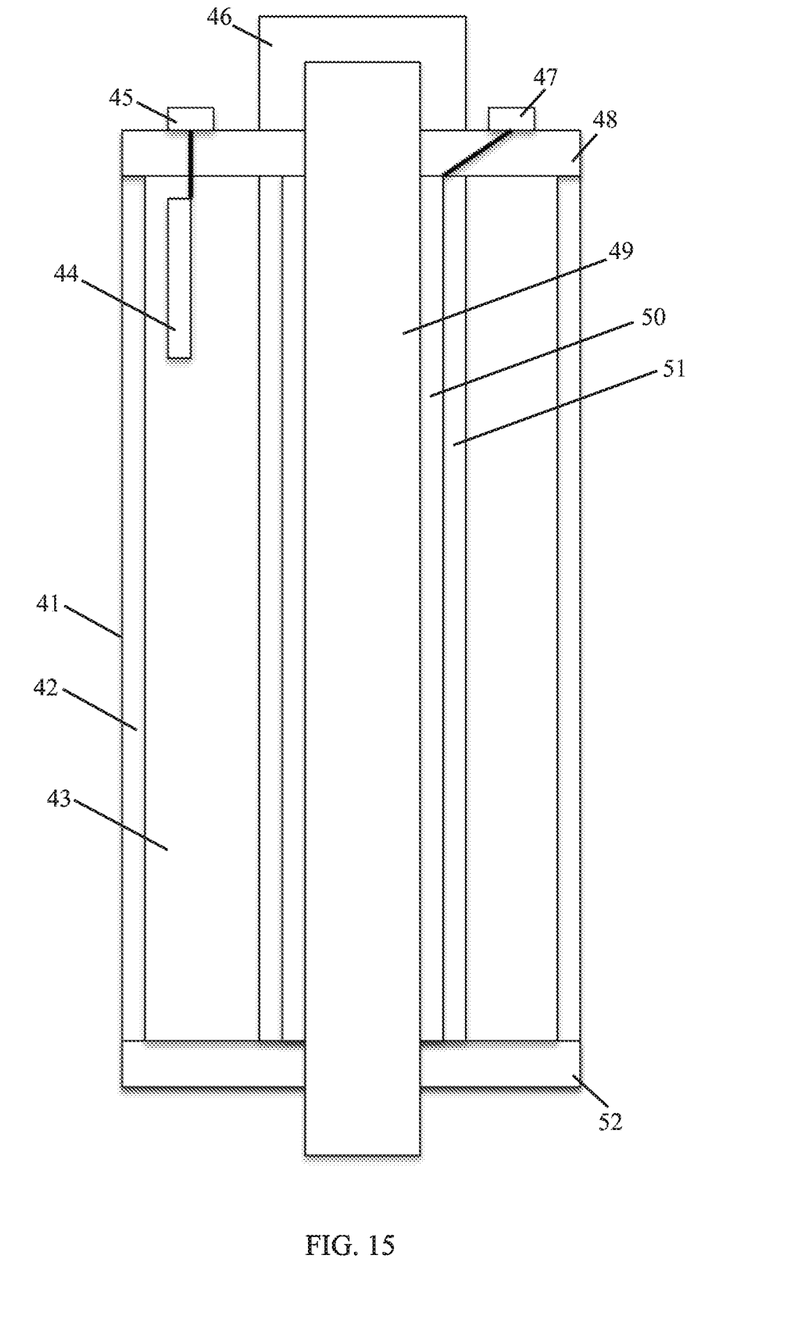
FIG. 15 shows a side cross section view drawing of an example of a single hollow tube bioelectrochemical system (BES) module in accordance with various embodiments of the present invention.

As understood from the example in FIG. 15, a system may include a perforated non-conductive tubular casing (41), a, course granular anode (42), a fine granular anode material (43), a conductive connector (44) to the granular anode material, a lead or connecting receptacle (45) for connecting a load to the anode, a connecter (46) fitting to connect add-ons (e.g., second module), a lead or connecting receptacle (47) for connecting a load to the cathode, a support (48) and even a seal for encasing electrodes, a central hollow perforated tube (49), a cathode material (50) with or without catalyst and perhaps with a waterproof coating, an electrode separator (51), and perhaps even a support (52) and seal for encasing electrodes.

Figure 16:
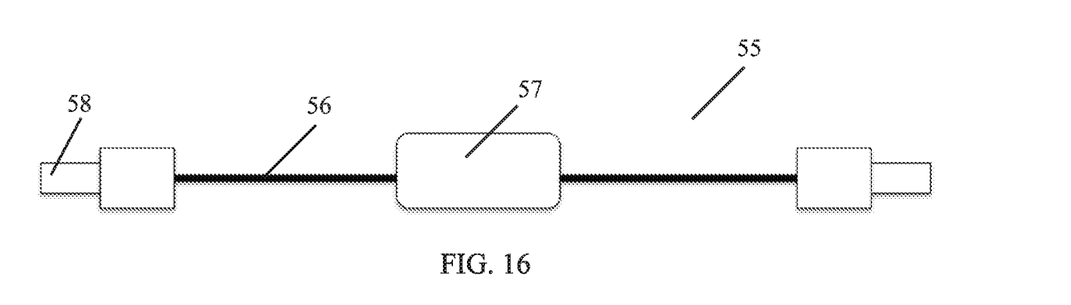
FIG. 16 shows an example load (e.g., resistor) and wire with conductive waterproof connectors at each end in accordance with various embodiments of the present invention. A load and wire may connect an anode to a cathode.

FIG. 16 is a non-limiting example of a transmission line (55) having a load (57) and wire (56) that may be constructed for quick plug-in to an anode and cathode receptacles. In some embodiments, a transmission line may have conductive waterproof connectors (58) at each end. In embodiments, a resistance of the load or resistor may range from about 0 to about 10,000 ohm; a voltage may range from between about 0.1 to about 380 volts; and perhaps even a current may range between about 0.001 mA to about 5 A.

In an embodiment of the present invention, a BES may include a graphite rod as anode and a carbon clothe as cathode. A test with this system provided $H_2$ as the predominant product that accumulated to about 110.8 mmol over about 30 days. The average production rate was about 36.9 mmol/L/day. No obvious $CH_4$ production was observed. Gradual physical mass loss of the graphite anode and increased turbidity and color of the solution were observed in the reactor. The solutions contain the exfoliated GO sheets and the supernatant exhibited blackish brown color. A maximum anode potential of about +1.6 V (vs. SHE) was observed in the BES reactor during operation, while the anode potential in the abiotic control ranged from about +0.71 to about +0.98 V (vs. SHE) despite a same cathode potential (about −0.6 V vs. SHE) that was poised on both reactors. The exfoliation rate of graphite anode was measured at about 388 mg-GO/L (reactor solution volume)/day.

As part of some of the embodiments of the present invention, presence and proper localization of a viable mixture of microorganisms, mainly bacteria, is important for the BES to function properly and even produce GO and H2 on anode and cathode vicinities, respectively. In some embodiments, biomass may be added in a reactor. For example, in one of the testing BES reactors, the bacterial genus *Pseudomonas* is the dominant population on the graphite anode (about 74%). Other major populations include *Rhodococcus, Ralstonia*, and *Propionibacterium*, which accounted for about 7%, about 4% and about 3% of the total composition, respectively (see FIG. 7). Other 90 genera making up less than about 1% of total composition were found with combined total abundance of about 7%. There were about 5% novel genera that had not been identified yet. Some species of *Pseudomonas*, such as *P. aeruginosa, P. alcaliphila* and *P. putida*, can self-excrete redox mediators to transfer electrons to the electrode. Among *Pseudomonas* population, the majority of sequences (about 75.3%) were closely similar to *P. syringae* (about 100% similarity).

Figure 17:
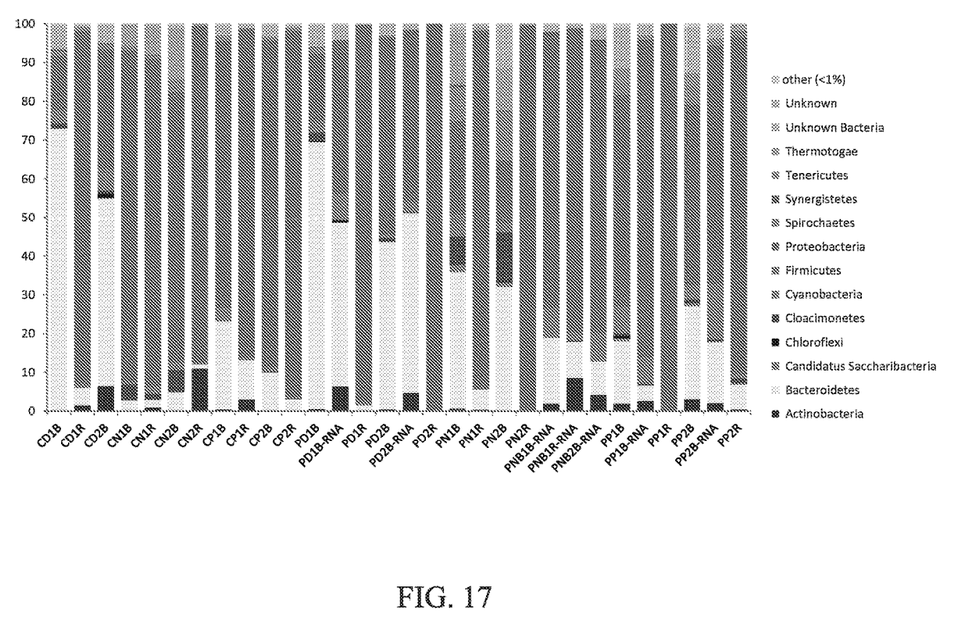
FIG. 17 shows an example bacterial community composition in a BES. Bacteria making up less than 1% of total composition are classified as "others".
Figure 18:
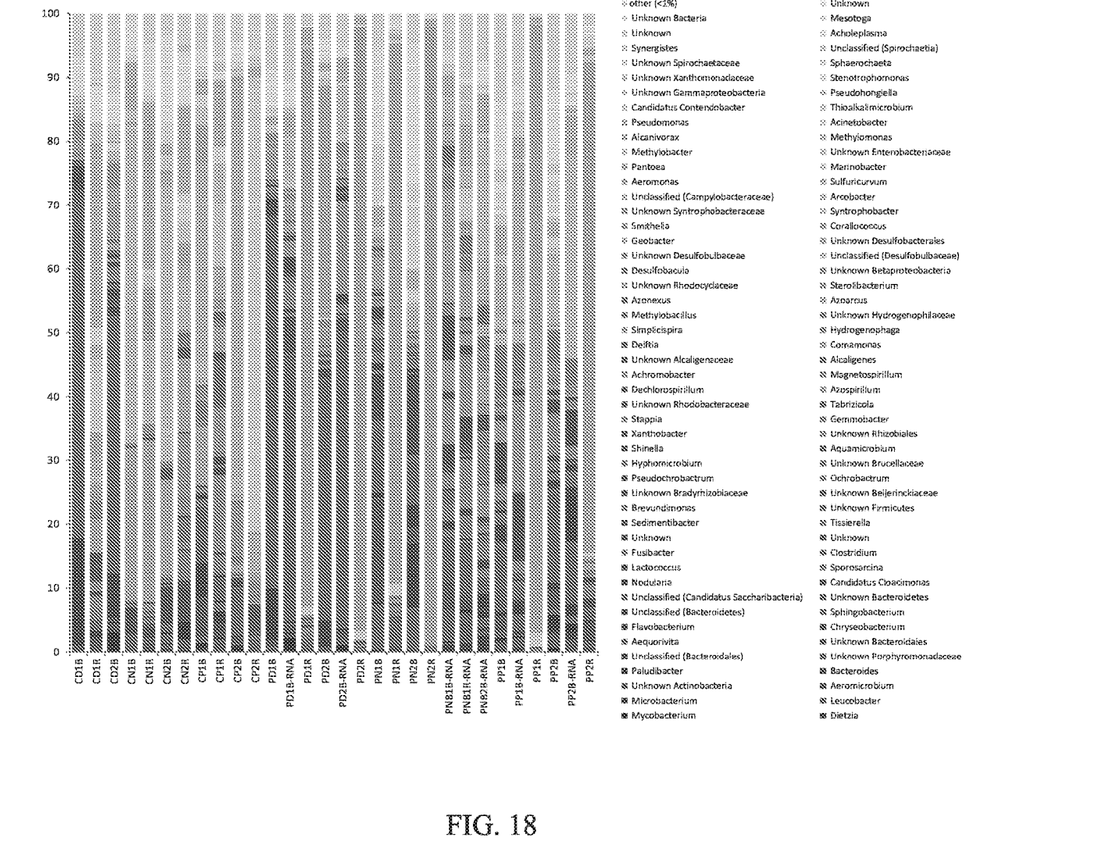
FIG. 18 shows another example of a bacterial community composition in a BES. Bacteria making up less than 1% of total composition are classified as "others".
Figure 19:
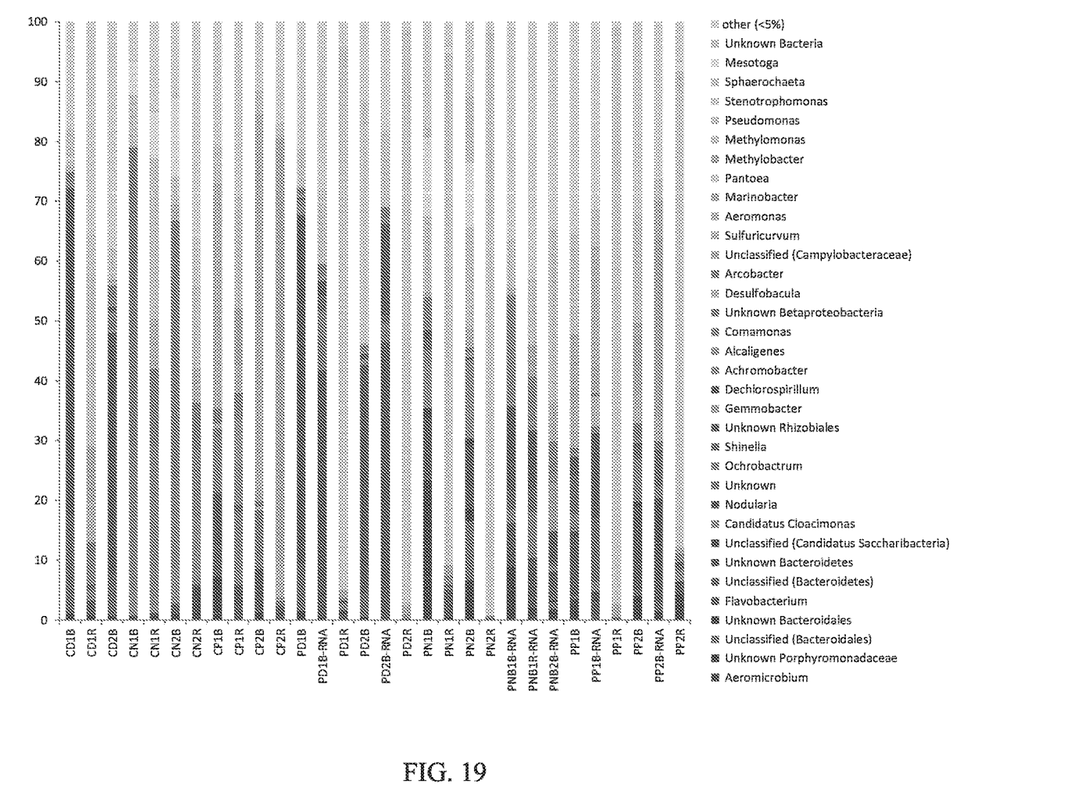
FIG. 19 shows another example of a bacterial community composition in a BES. Bacteria making up less than 5% of total composition are classified as "others".

In one test, a bacterial community on the cathode had a higher diversity than that on the anode. In addition to phylum Proteobacteria (anode about 85%, cathode about 56%), the community on the cathode was also dominated by Firmicutes (about 15%) and *Bacteroidetes* (about 20%), which were rarely found on the anode. Firmicutes was reported to be electrochemically active though the majority of such bacteria are known as Proteobacteria[35]. *Delftia* (about 11%), *Clostridium* (about 9%), *Alicycliphilus* (about 4%) and *Chryseobacterium* (about 12%) may be the dominant genera on the cathode. For *Clostridium*, all the sequences were closely similar to *C. carboxidivorans* (about 100% similarity), an anaerobic solvent-producing bacteria, which can grow autotrophically using $H_2/CO_2$ or CO with acetate, ethanol, butyrate and butanol as end products. A bacterial community may be diverse. The genus *Pseudomonas* was about 74% of community from a past test. In a recent study, *Pseudomonas* is about 0.2-29% of the community (DNA), and about 0.7-6.7% of the active community (RNA). Phylum-level diversity (very broad) may be much more diverse. In a previous work, the main phyla were Proteobacteria and Actinobacteria at an anode and Proteobacteria, Firmicutes, and *Bacteroidetes* at a cathode. In some examples, bacteria used in a BES reactor may include, but is not limited to Thermotogae, Tenericutes, Synergistetes, Spirochaetes, Proteobacteria, Firmicutes, Cyanobacteria, Cloacimonetes, Chloroflexi, *Candidatus Saccharibacteria, Bacteroidetes, Actinobacteria*, and any combination thereof, or the like. (see FIG. 17). In another example, bacteria used in a BES reactor may include, but is not limited to, *Mesotoga, Sphaerochaeta, Stenotrophomonas, Pseudomonas, Methylomonas, Methylobacter, Pantoea, Marinobacter, Aeromonas, Sulfuricurvum, Campylobacteraceae, Arcobacter, Desulfobacula, Betaproteobacteria, Comamonas, Alcaligenes, Achromobacter, Dechlorospirillum, Gemmobacter, Rhizobiales, Shinella, Ochrobactrum, Nodularia, Candidatus Cloacimonas, Candidatus Saccharibacteria, Bacteroidetes, Bacteroidetes, Flavobacterium, Bacteroidales, Bacteroidales, Porphyromonadaceae, Aeromicrobium*, and any combination thereof, or the like. (See FIG. 19)

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "collector" should be understood to encompass disclosure of the act of "collecting"—whether explicitly discussed or not—and, conversely, were there effectively disclosure of the act of "collecting", such a disclosure should be understood to encompass disclosure of a "collector" and even a "means for collecting." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the below list of references in the information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

| I. US PATENT APPLICATION PUBLICATIONS | | | |
|---|---|---|---|
| 20140315046 | A1 | 2014 Oct. 23 | Yoshida et al. |
| 20160022827 | A1 | 2016 Jan. 28 | Chan et al. |

| II. FOREIGN REFERENCE DOCUMENTS | | | | |
|---|---|---|---|---|
| 2012/167218 | WO | A2 | 2012 Dec. 6 | Nickel |

| III. NON PATENT LITERATURE DOCUMENTS |
|---|
| Park, Sungjin and Rodney Ruoff, Chemical methods for the production of graphenes. Nature Nanotechnology vol. 4, Review Article, published 29 Mar. 2009. 9 pages. |
| Lu, L et al., Graphene oxide and H2 production from bioelectrochemical graphite oxidation. Scientific Reports. www.nature.com/scientificreports, published 17 Nov. 2015. 11 pages. |
| Lu, L, et al. Supplementary Information for Graphene oxide and H2 production from bioelectrochemical graphite oxidation., published 17 Nov. 2015. 6 pages. |
| US Provisional Application No. 62/249,227, filed Oct. 31, 2015. First Named Inventor: Song Jin. |

Thus, the applicant(s) should be understood to have support to claim and make a statement of invention to at least: i) each of the scrubber devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim v. Cannon Avent Group*, PLC, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 25 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A bioelectrochemical method for producing graphene oxide comprising the steps of:
   providing at least one biochemical reactor;
   providing at least one graphite containing anode and at least one cathode in each of said at least one biochemical reactor;
   wherein said at least one cathode comprises a conductive material;
   connecting a load between said at least one graphite containing anode and said at least one cathode with a transmission line;
   providing at least one direct current electricity source connected to said transmission line;
   providing at least one microbial population in each of said at least one biochemical reactor;
   interacting said at least one graphite containing anode with said at least one microbial population resulting in production of graphene oxide, carbon dioxide ($CO_2$) and electrons;
   transferring said electrons from said at least one graphite containing anode to said at least one cathode via said transmission line;
   microbiologically reducing protons and said carbon dioxide ($CO_2$) at said at least one cathode resulting in production of $H_2$ and organic compounds; and
   collecting said graphene oxide from said at least one biochemical reactor.

2. The bioelectrochemical method for producing graphene oxide according to claim 1 wherein said at least one graphite containing anode comprises a configuration chosen from a rod, pellets, powder suspension, liquid suspension, and any combination thereof.

3. The bioelectrochemical method for producing graphene oxide according to claim 1 wherein said at least one graphite containing anode further comprises a material chosen from coal, coke, and any combination thereof.

4. The bioelectrochemical method for producing graphene oxide according to claim 1 wherein said at least one microbial population is chosen from aerobic microorganisms, facultative microorganisms, obligate anaerobic microorganisms, and any combination thereof.

5. The bioelectrochemical method for producing graphene oxide according to claim 1 wherein said at least one microbial population is chosen from Thermotogae, Tenericutes, Synergistetes, Spirochaetes, Proteobacteria, Firmicutes, Cyanobacteria, Cloacimonetes, Chloroflexi, *Candidatus Saccharibacteria*, Bacteroidetes, Actinobacteria, and any combination thereof.

6. The bioelectrochemical method for producing graphene oxide according to claim 1 wherein said step of providing said at least one microbial population comprises the steps of:
   providing said at least one microbial population at said at least one graphite containing anode, wherein said at least one microbial population is chosen from Proteobacteria, Actinobacteria, and a combination thereof; and
   providing said at least one microbial population at said at least one cathode, wherein said at least one microbial population is chosen from Proteobacteria, Firmicutes, Bacteroidetes, and any combination thereof.

7. The bioelectrochemical method for producing graphene oxide according to claim 1 wherein said at least one biochemical reactor is chosen from a sealed container, pit, in ground void, aboveground pit, coal seam, coal pile, direct insertion, borehole insertion, trench insertion, and any combination thereof.

8. The bioelectrochemical method for producing graphene oxide according to claim 1 wherein said step of collecting said graphene oxide from said at least one biochemical reactor comprises the step of collecting said graphene oxide, graphene, and graphite oxide from said at least one biochemical reactor.

9. The bioelectrochemical method for producing graphene oxide according to claim 1 and further comprising the step of providing at least one hollow tube in said at least one biochemical reactor.

10. The bioelectrochemical method for producing graphene oxide according to claim 9 wherein said hollow tube comprises a perforated hollow tube.

11. The bioelectrochemical method for producing graphene oxide according to claim 9 wherein said hollow tube is made of a material chosen from plastic, polyvinyl chloride, polymethyl methacrylate, fiberglass, high-density polytetrafluoroethylene, and any combination thereof.

12. The bioelectrochemical method for producing graphene oxide according to claim 9 and further comprising the step of providing said at least one graphite containing anode at an outermost layer surrounding said hollow tube.

13. The bioelectrochemical method for producing graphene oxide according to claim 9 and further comprising the step of providing said at least one cathode at an innermost layer surrounding said hollow tube.

14. The bioelectrochemical method for producing graphene oxide according to claim 9 wherein said at least one cathode directly contacts said hollow tube.

15. The bioelectrochemical method for producing graphene oxide according to claim 1 wherein said at least one cathode comprises a material chosen from fine stainless steel mesh, stainless steel foam, iron filings, stainless steel rod, mesh, stainless steel wool, stainless steel foam, stainless steel brush, carbon cloth, activated carbon, carbon paper, and any combination thereof.

16. The bioelectrochemical method for producing graphene oxide according to claim 1 wherein said at least one cathode is coated with a catalyst.

17. The bioelectrochemical method for producing graphene oxide according to claim 16 wherein said catalyst comprises a material chosen from platinum/carbon (Pt/C) catalyst, iridium catalyst, zinc oxide, lead oxides, titanium oxides (rutile), and any combination thereof.

18. The bioelectrochemical method for producing graphene oxide according to claim 1 wherein said at least one cathode comprises a waterproof and air permeable coating.

19. The bioelectrochemical method for producing graphene oxide according to claim 18 wherein said waterproof and permeable coating is chosen from polytetrafluoroethylene, poly(dimethylsiloxane), and a combination thereof.

20. The bioelectrochemical method for producing graphene oxide according to claim 1 and further comprising the steps of:
providing a load resistance between 0 to about 10,000 ohm;
providing a voltage between about 0.1 to about 380 volts; and
providing a current between about 0.001 mA to about 5 A in said biochemical reactor.

21. The bioelectrochemical method for producing graphene oxide according to claim 1 and further comprising the step of separating said graphene oxide from said at least one graphite containing anode in said biochemical reactor.

22. The bioelectrochemical method for producing graphene oxide according to claim 1 and further comprising the step of providing at least one enzyme in said biochemical reactor.

* * * * *